United States Patent
Drew et al.

(10) Patent No.: US 9,486,635 B2
(45) Date of Patent: Nov. 8, 2016

(54) MEDICAL DEVICE INCLUDING SETUP OPTION REPORTING

(71) Applicant: Physio-Control, Inc., Redmond, WA (US)

(72) Inventors: Kevin C. Drew, Snohomish, WA (US); James S. Neumiller, Redmond, WA (US)

(73) Assignee: PHYSIO-CONTROL, INC., Redmond, WA (US)

(*) Notice: Subject to any disclaimer, the term of this patent is extended or adjusted under 35 U.S.C. 154(b) by 0 days.

(21) Appl. No.: 15/048,581

(22) Filed: Feb. 19, 2016

(65) Prior Publication Data

US 2016/0166839 A1      Jun. 16, 2016

Related U.S. Application Data

(60) Continuation of application No. 14/566,457, filed on Dec. 10, 2014, now Pat. No. 9,265,959, which is a continuation of application No. 14/182,548, filed on Feb. 18, 2014, now Pat. No. 9,067,077, which is a division of application No. 13/308,329, filed on Nov. 30, 2011, now Pat. No. 8,694,100.

(60) Provisional application No. 61/418,369, filed on Nov. 30, 2010.

(51) Int. Cl.
*A61N 1/39*      (2006.01)
*A61N 1/372*     (2006.01)
*A61B 5/021*     (2006.01)
*A61B 5/044*     (2006.01)
*A61N 1/37*      (2006.01)
*A61B 5/145*     (2006.01)

(52) U.S. Cl.
CPC .......... *A61N 1/37252* (2013.01); *A61B 5/021* (2013.01); *A61B 5/044* (2013.01); *A61B 5/14542* (2013.01); *A61N 1/3706* (2013.01); *A61N 1/37247* (2013.01); *A61N 1/3937* (2013.01); *A61N 1/3993* (2013.01)

(58) Field of Classification Search
None
See application file for complete search history.

(56) References Cited

U.S. PATENT DOCUMENTS

| | | | |
|---|---|---|---|
| 6,021,491 | A | 2/2000 | Renaud |
| 6,539,947 | B2 | 4/2003 | Boies et al. |
| 6,662,052 | B1 | 12/2003 | Sarwal et al. |
| 8,065,397 | B2 | 11/2011 | Taylor et al. |

*Primary Examiner* — Brian T Gedeon
(74) *Attorney, Agent, or Firm* — Marger Johnson

(57) ABSTRACT

A medical device for use with a patient is described. The medical device includes a component for administering a treatment to the patient or receiving data of the patient. The component is configured to operate according to an internal setting. The medical device also includes a user interface through which a user can modify the internal setting, as well as a settings signature generator for generating a settings signature that represents a present state of the internal setting. A gateway is also provided for communicating a version of the settings signature out of the medical device.

30 Claims, 5 Drawing Sheets

COMPONENTS OF EXTERNAL DEFIBRILLATOR

*MEDICAL DEVICE*

COMPONENTS OF EXTERNAL DEFIBRILLATOR

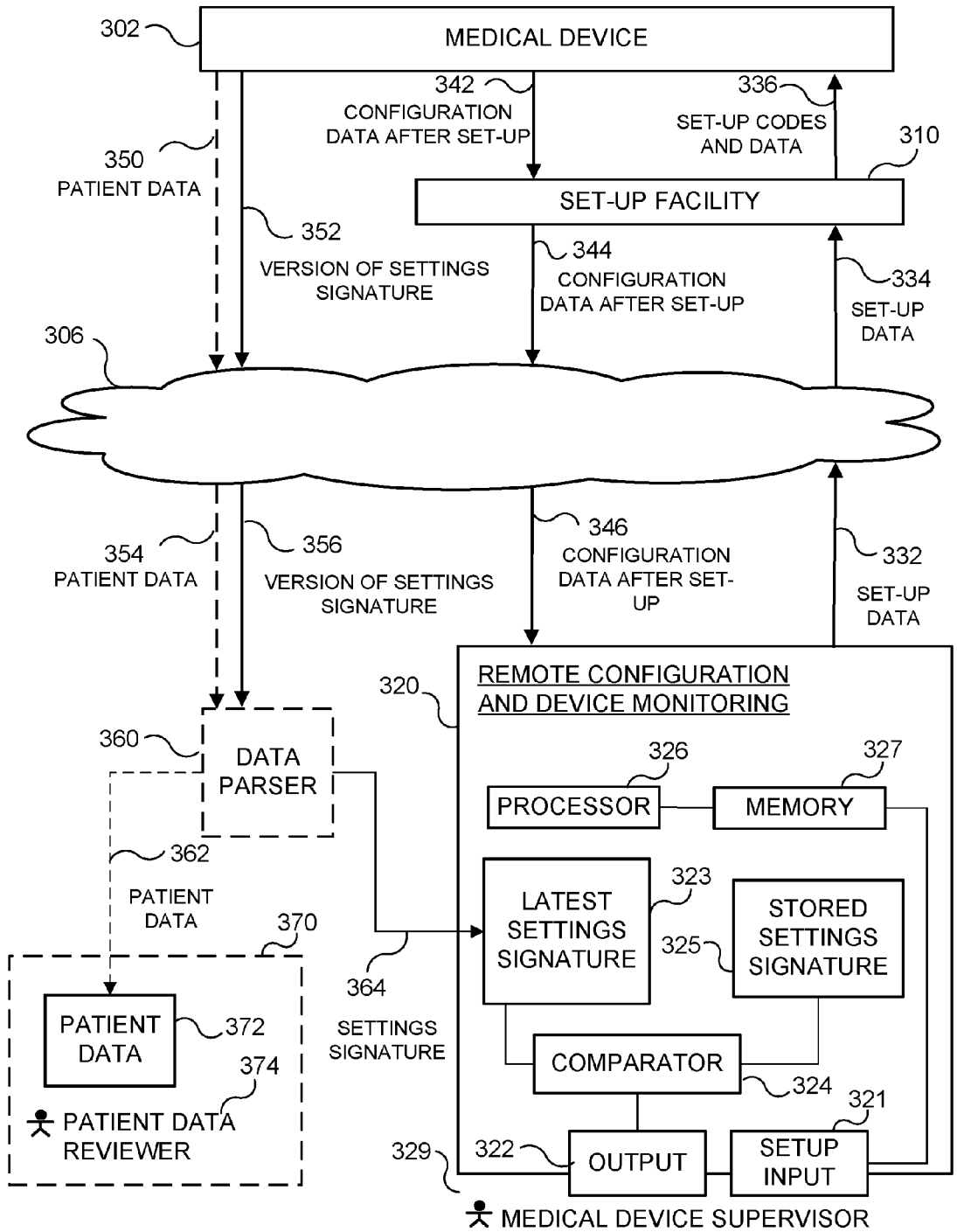
FIG. 3 REMOTE CONFIGURATION & DEVICE MONITORING SYSTEM

| FUNCTION OF COMPONENT | SETTING(S) FOR FUNCTION |
|---|---|
| DEFIBRILLATOR PROTOCOL | WHICH TREATMENT PROTOCOL TO USE |
| MENU | TIMEOUT, LANGUAGE, SUMMARY |
| ENERGY DELIVERY | ENERGY LEVEL |
| PACER | RATE, CURRENT |
| ADVISORY MODE | MOTION DETECT, PRE-SHOCK CPR |
| METRONOME SETTING | SCHEDULE |
| TRANSMISSION MODE | WIRELESS, SITENAME |
| ALARM MODE | ON/OFF, VOLUME |
| PASSCODE | SET/DELETE |
| PRINTER MODES | AUTO, ECG MONITOR MODES |
| ECG MODES | CONTINUOUS, UNITS |
| PASSWORD PROTECTION | ON/OFF |
| PATIENT ANALYSIS MODE | AUTOMATIC/MANUAL |
| CPR TIMER | DURATION |
| PATIENT MONITOR | UNITS OF MEASURE, NUMBER OF CHANNELS, MONITOR MODE |

FIG. 4

*FUNCTIONS AND CORRESPONDING SETTINGS*

METHODS OF DETECTING SETUP OPTION CHANGE IN MEDICAL DEVICE

MEDICAL DEVICE INCLUDING SETUP OPTION REPORTING

CROSS REFERENCE TO RELATED PATENT APPLICATIONS

This patent application claims priority to U.S. patent application Ser. No. 14/566,457, titled MEDICAL DEVICE INCLUDING SETUP OPTION REPORTING, filed on Dec. 10, 2014, which claims priority to U.S. Pat. No. 9,067,077, titled MEDICAL DEVICE INCLUDING SETUP OPTION REPORTING, filed on Feb. 18, 2014, which claims priority to U.S. Pat. No. 8,694,100, titled MEDICAL DEVICE INCLUDING SETUP OPTION REPORTING, filed on Nov. 30, 2011, which claims benefit of U.S. Provisional Patent Application Ser. No. 61/418,369, titled DEVICE SETUP CHANGE DETECTION, filed on Nov. 30, 2010, the disclosures of which are hereby incorporated by reference for all purposes.

FIELD

This invention generally relates to medical devices and related communications systems.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

Medical devices typically have several option settings that govern how particular components or functions within the medical device operate. For example, an audible alarm may be selectively enabled and a volume controlled through a user interface. Giving a user of the medical device control of how the medical device functions allows the user to tailor operation of the device for particular situations or operating conditions. A medical director, for example within an emergency medical service, may have the responsibility for ensuring medical devices are properly configured and operated. Giving the user an ability to modify the configuration of the medical device through the setup options of the device, while convenient for the user, may allow the user to change a configuration of the device contrary to the direction of the medical director or other party. Embodiments of the invention address this and other limitations in the prior art.

BRIEF SUMMARY

The present description gives instances of devices, systems, software and methods, the use of which may help overcome problems and limitations of the prior art.

In one embodiment, a medical device for use with a patient includes a component for either administering a treatment to the patient or receiving data of the patient. The component is configured to operate according to an internal setting. The medical device also includes a user interface through which a user can modify the internal setting and a settings signature generator for generating a settings signature that represents a present state of the internal setting. The medical device further includes a gateway for communicating a version of the settings signature out of the medical device.

Another embodiment is directed to a method for use with a medical device, in which the medical device has a component for administering a treatment to a patient or for receiving data of the patient. The method includes receiving a version of the settings signature generated by the medical device over a communication network and outputting a warning if it is determined from the settings signature that the internal setting deviates from an expected state of the internal setting.

An advantage over the prior art is that a medical director or other party may be informed when the user changes a setting on the medical device.

These and other features and advantages of this description will become more readily apparent from the following Detailed Description, which proceeds with reference to the drawings, in which:

BRIEF DESCRIPTION OF THE DRAWINGS

FIG. 3 is a system diagram of a communication system that incorporates the medical device, such as the medical device of FIG. 1, according to embodiments of the invention.

FIG. 4 is a chart illustrating example component functions and example settings that may be stored in the medical device of FIG. 1.

DETAILED DESCRIPTION

As has been mentioned, the present description is about medical devices and devices, software and methods for reporting changes in setup options of the medical device. Embodiments are now described in more detail.

Figure 1:
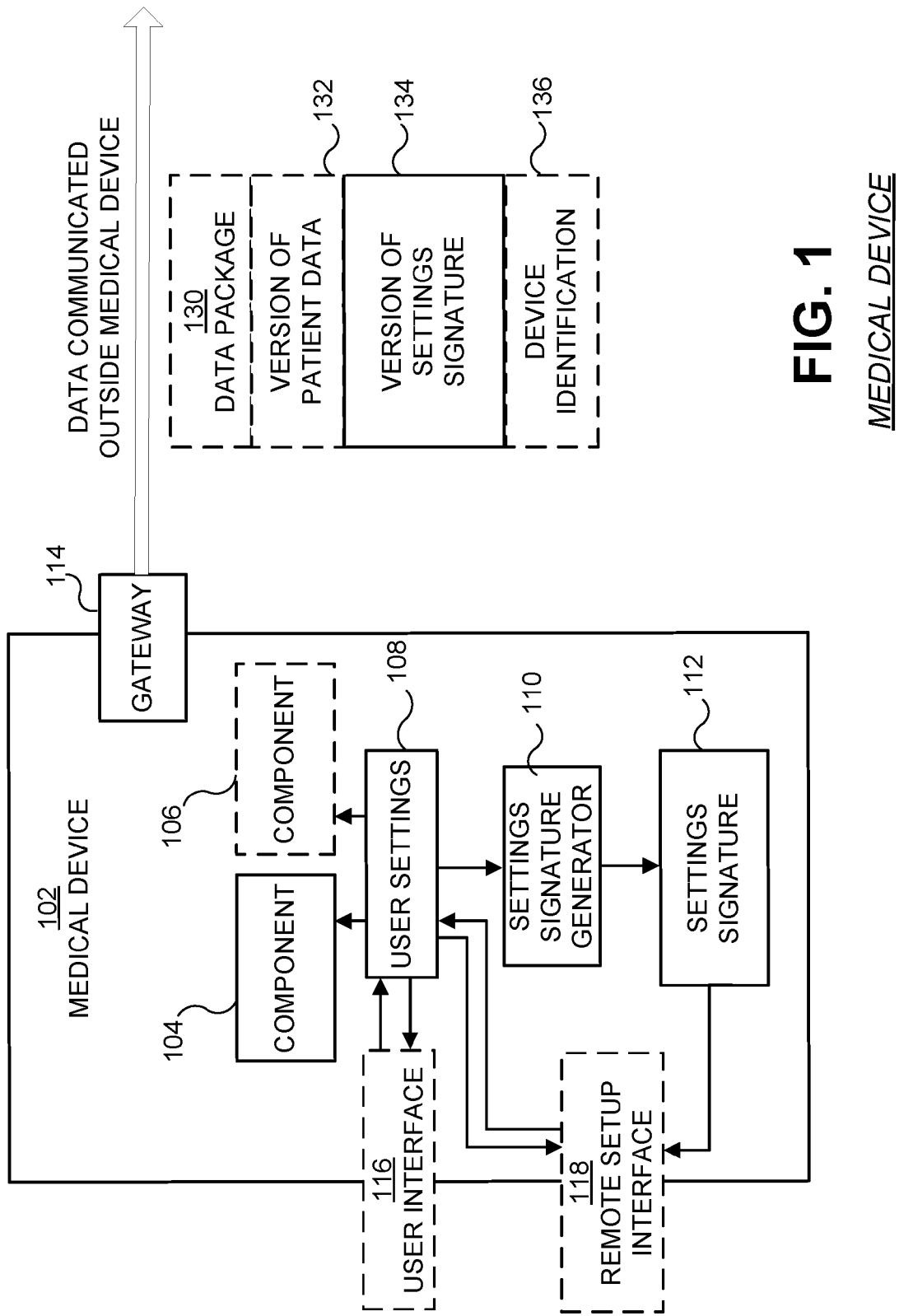
FIG. 1 is a functional block diagram of a medical device that generates a setup signature according to embodiments.

FIG. 1 is a functional block diagram of a medical device that generates a setup signature according to embodiments. A medical device 102 is for use with a patient, not illustrated. In some embodiments the patient is experiencing cardiac arrest and the medical device is a defibrillator. The medical device 102 includes a component 104 for administering a treatment to the patient or for receiving data of the patient. For example, the component 104 may be an energy storage device for providing an electric charge to the patient. Or, in another example, the component 104 may be a non-invasive blood pressure monitor. The component 104 is configured to operate according to an internal setting or settings, as described in detail below. The internal setting is stored, along with internal settings for other, optional, components, such as a component 106, in user settings 108. The user settings 108 may be, for example, a memory that is internal to the medical device 102. The medical device 102 also includes a user interface 116, such as a touchscreen, through which a user can modify the user settings 108.

A settings signature generator 110 generates a settings signature 112 that represents a present state of internal settings in the user settings 108. For example, the settings signature generator 110 may perform a computer function on data in the user settings 108 to compute the settings signature 112. In some embodiments, the settings signature 112 is a cyclic redundancy check of a memory block that stores the user settings 108. In other embodiments the settings signature 112 is derived from a hash function of at least a portion of a memory block storing the user settings 108. The hash function may be a message digest function, such as MD5, for example. In other embodiments, the settings signature 112 is merely a coded version of the user settings 108. Depending on the code, particular settings of the medical device 102 may be able to be decoded and discerned merely by analyzing the coded version of the settings signature 112. For example, in such an embodiment, a receiver could determine an energy setting of the particular medical device by analyzing the version of the settings signature 112 in which the energy setting is stored. Typically, having a settings signature 112 that can be decoded will be larger, take more storage, and require more communication bandwidth than a settings signature that merely identifies a current set of user settings 108.

The medical device 102 may generate the settings signature 112 on a regular schedule. For example, the settings signature generator 110 may be structured to generate the settings signature 112 substantially periodically. In other embodiments, the settings signature generator 110 may be structured to generate the settings signature 112 in response to an external query, such as a query through a remote setup interface 118, described below.

The medical device 102 includes a gateway 114 for communicating a version of the settings signature out of the medical device. The data sent from the device may be a predefined data structure, such as a data package 130, which includes a version of the settings signature 134. The version of the settings signature 134 is derived from the settings signature 112, and in some embodiments may be identical to the settings signature 112. In other embodiments, the version of the settings signature 134 is a packetized version of the settings signature 112 especially where the settings signature 112 is too long to fit in a single packet.

As illustrated in FIG. 1, the data package 130 may optionally include a version of patient data 132, so that the patient data is communicated out of the medical device 102 in conjunction with the version of the settings signature 134. As described above, one or more of the components 104, 106 of the medical device 102 may gather data from a patient. The data package 130 may optionally include some or all of the patient data gathered in a version of the patient data 132. The data package 130 may also optionally include a device identification 136, which may be transmitted from the gateway 114 of the medical device 102. This is described in more detail below, with reference to FIG. 3. In some embodiments the predefined data structure, such as the data package 130, includes a section for device data, within which the version of the settings signature 134 and the optional device identification 136 is stored.

The medical device may send the version of the settings signature 134 on a regular schedule. For example, in some embodiments, the gateway 114 may be structured to communicate the version of the settings signature 134 substantially periodically. In other embodiments, the gateway 114 may be structured to communicate the version of the settings signature 134 in response to an event. The event may be an external query, for example, received through the remote setup interface 118 or other port. The external query to cause the version of the settings signature 134 to be sent from the medical device 102 may be performed before or during the time that the medical device is used on the patient. In other embodiments, the device 102 is programmed so that the event is the taking of an ECG of a patient.

Figure 2:
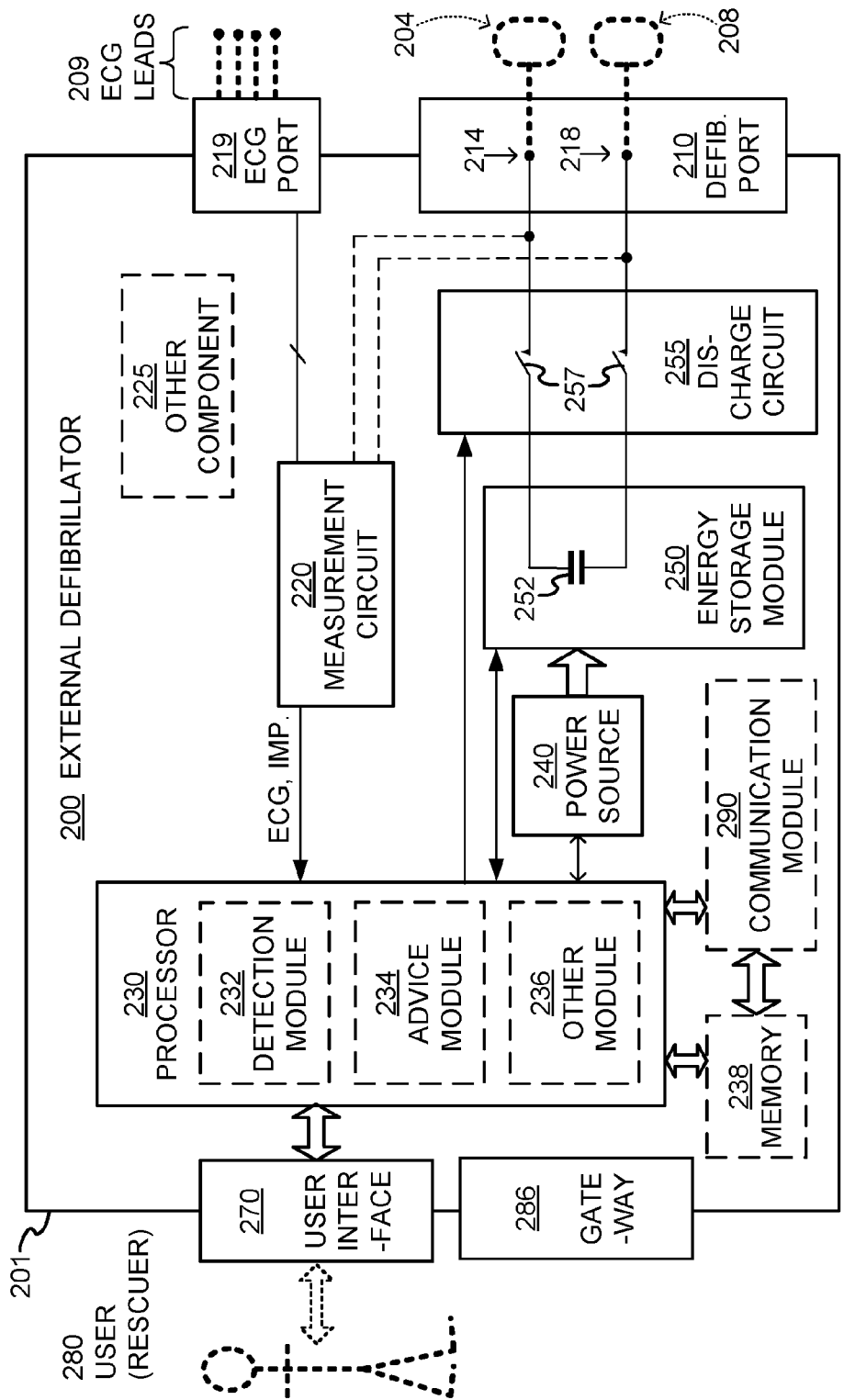
FIG. 2 is a diagram showing components of an external defibrillator, which may be an example medical device of FIG. 1, according to embodiments.

FIG. 2 is a diagram showing components of an external defibrillator 200 made according to embodiments. The external defibrillator 200 may be an embodiment of the medical device 102 described with reference to FIG. 1.

External defibrillator 200 is intended for use by a user 280, who would be the rescuer. Defibrillator 200 typically includes a defibrillation port 210, such as a socket in housing 201. Defibrillation port 210 includes nodes 214, 218. Defibrillation electrodes 204, 208, can be plugged in defibrillation port 210, so as to make electrical contact with nodes 214, 218, respectively. It is also possible that electrodes can be connected continuously to defibrillation port 210, etc. Either way, defibrillation port 210 can be used for guiding via electrodes to a person an electrical charge that has been stored in defibrillator 200.

If defibrillator 200 is actually a defibrillator-monitor, then it will typically also have an ECG port 219 in housing 201, for plugging in ECG leads 209. ECG leads 209 can help sense an ECG signal, e.g. a 12-lead signal, or from a different number of leads. Moreover, a defibrillator-monitor could have additional ports (not shown), and an other component 225 for the above described additional features, such as patient signals. The other component 225 may be embodiments of components 104, 106 of FIG. 1.

Defibrillator 200 also includes a measurement circuit 220. Measurement circuit 220 receives physiological signals from ECG port 219, and also from other ports, if provided. These physiological signals are sensed, and information about them is rendered by circuit 220 as data, or other signals, etc.

If defibrillator 200 is actually an AED, it may lack ECG port 219. Measurement circuit 220 can obtain physiological signals through nodes 214, 218 instead, when defibrillation electrodes 204, 208 are attached to a person. In these cases, a person's ECG signal can be sensed as a voltage difference between electrodes 204, 208. Plus, impedance between electrodes 204, 208 can be sensed for detecting, among other things, whether these electrodes 204, 208 have been inadvertently disconnected from the person.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232, which senses outputs of measurement circuit 220. Detection module 232 can include a VF detector. Thus, the person's sensed ECG can be used to determine whether the person is experiencing VF.

Another such module in processor 230 can be an advice module 234, which arrives at advice based on outputs of detection module 232. Advice module 234 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 200 may further issue prompts for it, and so on. these modules 232, 234 may be embodiments of components 104, 106 of FIG. 1.

Processor 230 can include additional modules, such as module 236, for other functions, such as the settings signature generator 110 of FIG. 1. In addition, if other component 225 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, nonvolatile memories (NVM), read-only memories (ROM), random access memories (RAM), any combination of these, and so on. Memory 238, if provided, can include programs for processor 230, and so on. The programs can be operational for the inherent needs of processor 230, and can also include protocols and ways that decisions can be made by advice module 234. In addition, memory 238 can store prompts for user 280, etc. Moreover, memory 228 can store patient data. Memory 228 may also be a location in which the user settings 108 of FIG. 1 are stored. Additionally, memory 228 may store the settings signature 112.

Defibrillator 200 may also include a power source 240. To enable portability of defibrillator 200, power source 240 typically includes a battery. Such a battery is typically implemented as a battery pack, which can be rechargeable or not. Sometimes, a combination is used, of rechargeable and non-rechargeable battery packs. Other embodiments of power source 240 can include AC power override, for where AC power will be available, and so on. In some embodiments, power source 240 is controlled by processor 230.

Defibrillator 200 additionally includes an energy storage module 250. Module 250 is where some electrical energy is stored, when preparing it for sudden discharge to administer a shock. Module 250 can be charged from power source 240 to the right amount of energy, as controlled by processor 230. In typical implementations, module 250 includes one or more capacitors 252, and so on.

Defibrillator 200 moreover includes a discharge circuit 255. Circuit 255 can be controlled to permit the energy stored in module 250 to be discharged to nodes 214, 218, and thus also to defibrillation electrodes 204, 208. Circuit 255 can include one or more switches 257. Those can be made in a number of ways, such as by an H-bridge, and so on.

Defibrillator 200 further includes a user interface 270 for user 280. User interface 270 can be made in any number of ways. For example, interface 270 may include a screen, to display what is detected and measured, provide visual feedback to the rescuer for their resuscitation attempts, and so on. Interface 270 may also include a speaker, to issue voice prompts, etc. Interface 270 may additionally include various controls, such as pushbuttons, keyboards, and so on. In addition, discharge circuit 255 can be controlled by processor 230, or directly by user 280 via user interface 270, and so on.

Defibrillator 200 can optionally include other components. For example, a communication module 290 may be provided for communicating with other machines. Such communication can be performed wirelessly, or via wire, or by infrared communication, and so on. This way, data can be communicated, such as patient data, incident information, therapy attempted, CPR performance, and so on.

Any of the components of the external defibrillator 200, such as those described above, may be embodiments of the components 104, 106 of FIG. 1, that operate according to user settings 108. In operation, the defibrillator 200 may generate a settings signature 112 of the user settings of the defibrillator, as described above with reference to FIG. 1. A version of the settings signature 134, may be communicated out of the defibrillator 200 through a gateway 286, in the manner described above with reference to FIG. 1.

FIG. 3 is a system diagram of a communication system that incorporates the medical device 102 of FIG. 1 or the defibrillator 200 of FIG. 2. An example process for setting up and monitoring a medical device is described below. A system 300 includes a medical device 302, which may be the same or similar to the medical device 102 of FIG. 1, or the external defibrillator 200 of FIG. 2, for instance. A setup facility 310 is coupled to the medical device 302, and passes data to and receives data from the medical device. In some embodiments the data may be transferred through the remote setup interface 118 illustrated in FIG. 1, although other ports could also be used. In some embodiments the setup facility 310 is a standalone process, such as a program running on a computer (not illustrated) used to set up the medical device 302. In other embodiments the setup facility 310 may be resident on or a part of the medical device 302 itself.

The setup facility 310 is coupled through a communication network 306, such as the internet or other appropriate network, to a remote configuration and device monitoring system 320. The remote configuration system 320 includes an output 322 and a setup input 321 for use by an individual, such as a medical device supervisor 329.

In setup operation, an individual, such as the medical device supervisor 329 provides setup specifications for the medical device 302, such as an initial set of user settings 108 (FIG. 1) to be stored in the medical device 302. The remote configuration system 320 sends setup data 332 through the communication network 306 to the setup facility 310. In FIG. 3 this is illustrated as setup data 332 leaving the remote configuration system 320, and setup data 334 being received by the setup facility 310. The setup facility 310 receives the setup data 334, then sends setup codes and data 336 used to configure the medical device 302 to the medical device. The medical device 302, then configures itself based on the received setup codes and data 336. For example, this may include storing an initial state of settings in the user settings, such as user settings 108 of FIG. 1. Thus in some embodiments, a medical device includes a remote setup interface 118 through which data can be received, and in which the medical device is structured to set the internal setting based on the data received through the remote setup interface.

After the medical device 302 is configured, the medical device generates a settings signature of the user settings, such as the settings signature 112 of FIG. 1. The signature, and perhaps other data such as an acknowledgement that the medical device 302 has been set up is sent to the setup facility 310. This is illustrated as 342. Then the setup facility 310 passes configuration data after setup 344 to the communication network 306, and further, illustrated as 346, to the remote configuration system 320. After the remote configuration system 320 receives configuration data after setup 346 from the medical device 302, the configuration system 320 stores a signature of the original setup as stored settings signature 325.

In monitoring operation, in general, the system 300 compares a settings signature sent from the medical device 302, such as through the gateway 114 (FIG. 1) or gateway 286 (FIG. 2) to the stored settings signature 325 stored just after setup. If the signatures match, then the medical device 302 is operating with the original user settings 108. If instead they don't match, that means that a user has adjusted the user settings of the medical device. A warning may then be generated and sent from the output 322. If multiple medical devices 302 are coupled to the system 300, the device identification 136 from a particular device may be used to ensure the correct latest settings signature 323 is being compared to the stored settings signature 325. In other embodiments, other device identification techniques may be employed.

The medical device 302 sends a version of the settings signature 352, which may be in a data packet similar to the data package 130 of FIG. 1. The version of the settings signature 352 is sent to the communication network 306, which then optionally passes the version of the settings signature 356 to an optional data parser 360. If present, the data parser 360 may split a version of patient data 354, which was sent as 350 from the medical device 302, from the version of the settings signature 356. Then patient data 372 may optionally be sent to a patient data reviewer 374, such as a doctor in a hospital.

The settings signature 364 is stored in the remote configuration and device monitoring system 320 as a latest settings signature 323. Then, the remote configuration and device monitoring system 330 periodically compares the latest settings signature 323 to the stored settings signature 325. If they do not match, a warning is generated and sent through the output 322.

With reference to FIGS. 2 and 3, embodiments of the invention include a system 300 for use with a medical device 302 having a component 250 for administering a treatment to a patient or a component 220 for receiving data of the patient. The system includes a processor 230 and a memory 238 storing instructions which, when executed by the processor result in sending a version of the settings signature 134, (FIG. 1) generated by the medical device 302 over a communication network 306; and outputting a warning if it is determined from the settings signature 323 that the internal setting deviates from an expected state of the internal setting 325. The system 300 determines the deviation by comparing the settings signature 323 to a previously stored signature of the internal setting 325, and generating the warning based on the comparison. In some embodiments, the remote configuration facility 320 stores instructions in a second memory 327 which, when executed by a second processor 326 result in specifying a particular setup configuration 332 of the internal setting and transmitting data 346 identifying the particular setup configuration to the medical device 302 across the communication network 306. As mentioned above, the version of the settings signature 352 may be sent from the medical device 302 periodically, or may be sent based on an event at the medical device 302. The system may also be structured to transmitting a query to the medical device 302, and the event that causes the medical device to send the version of the settings signature 352 is the receipt of the query at the medical device 302. In some embodiments, the warning from the output 322 of the remote configuration and device monitoring system 320 is communicated to an agency outside the medical device 302.

FIG. 4 is a chart illustrating example functions and example settings that may be stored in the medical device of FIG. 1. For example, in some embodiments, the component 104 of the medical device 102 is a defibrillator and the internal setting in the user settings 108 identifies a protocol of the defibrillator. The component 104 may be permissively accessed and the internal setting in the user settings 108 enables or disables the permissive access. In some embodiments the component 104 is an energy delivery component and the internal setting in the user settings 108 sets an energy delivery level. If the component 104 is a patient analyzer, the internal setting of the user settings 108 determines whether the patient analyzer is set to analyze a patient without user action. For example, some patient analyzers include a mode that automatically analyze a patient, while other modes require a user to perform particular actions, such as by initiating analysis by pressing a button.

In some embodiments the component 104 is a Cardio-Pulmonary Resuscitation timer and the internal setting of the user settings 108 determines a duration. In some embodiments the component 104 is a pacer and the internal setting of the user settings 108 describes a pacing rate. In some embodiments the component 104 is a metronome and the internal setting of the user settings 108 determines a metronome schedule. In some embodiments the component 104 is a pacer and the internal setting of the user settings 108 identifies a pacer current. In some embodiments the component 104 is a data transmitter and the internal setting of the user settings 108 describes a channel or address for transmission of data. For example, the medical device 102 may use a wireless version of the gateway 114, and the internal setting identifies how the wireless communication with the medical device 102 is established. In other embodiments the gateway 114 is connected to a communication network, and the internal setting identifies a destination communication address.

In some embodiments the component 104 is a carbon dioxide monitor or a blood pressure monitor and the internal setting of the user settings 108 describes the units of measure for the monitor. In some embodiments the component 104 is an alarm and the internal setting of the user settings 108 controls an alarm volume. In some embodiments the component 104 is a patient monitoring lead and the internal setting of the user settings 108 determines whether patient data will be transferred without user action.

In some embodiments the component 104 is an ECG display and the internal setting of the user settings 108 includes an operation mode of the display, or units of the ECG display. In some embodiments the component 104 is a printer and the internal setting of the user settings 108 includes a printer operation mode.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 5:
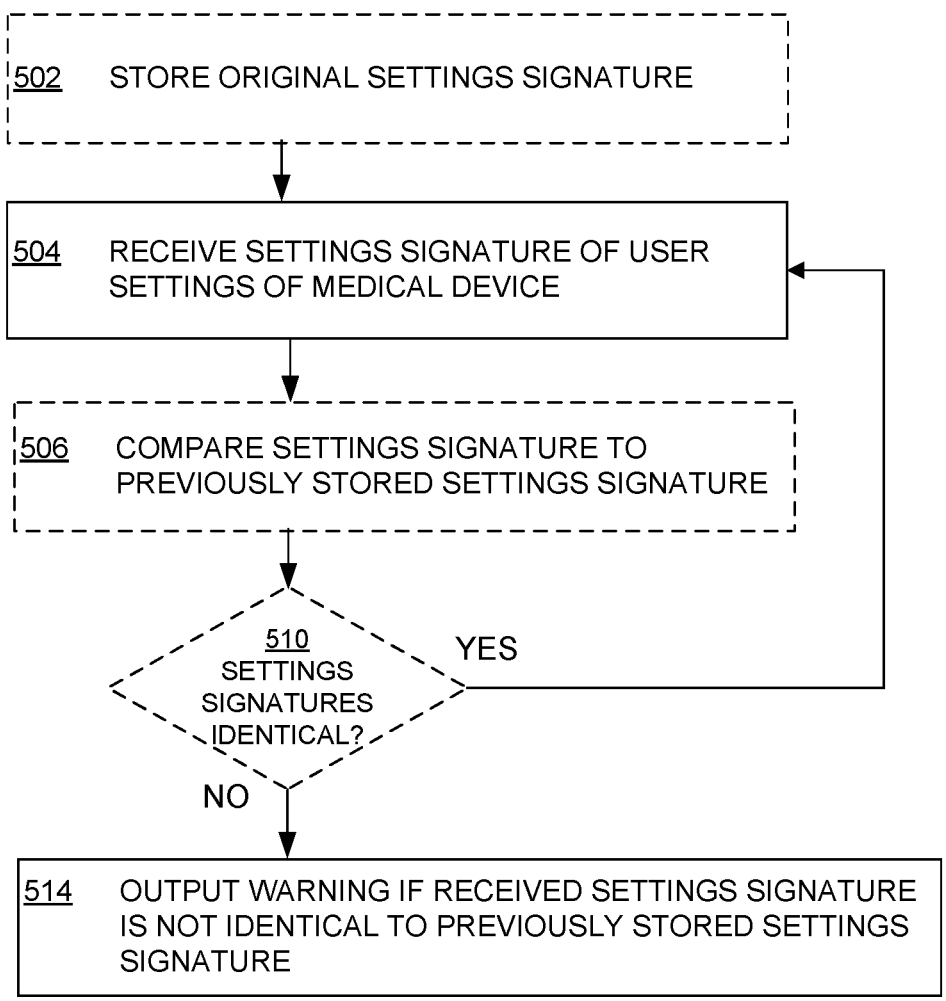
FIG. 5 is a flowchart illustrating example methods for detecting setup option change in a medical device according to embodiments.

FIG. 5 is a flowchart of example methods for detecting setup option change in a medical device according to embodiments. The method of flowchart 500 may be practiced by any of the portions of the system 300 illustrated in FIG. 3, which, in turn, may include the medical device 102 of FIG. 1 or external defibrillator 200 of FIG. 2. Particular components described below as performing various method processes are merely examples of where such processes may be performed, as various components within the system described above are capable of performing the described processes.

A flowchart 500 receives a settings signature of user settings of a medical device over a communication network at a process 504 when, for example, the remote configuration and device monitoring system 320 (FIG. 3) receives the settings signature 364 over the communication network 306. An optional process 502 stores the original settings signature. For example, the stored settings signature 325 of FIG. 3 that was specified when setting up the device may be stored in the remote configuration and device monitoring system 320, or elsewhere. As described above, the settings signature 364 may be sent periodically by the medical device 302, or it may be sent based on a particular request. Then, the flowchart 500 outputs a warning in a process 514 if it is determined from the settings signature 364 that the internal setting deviates from an expected state of the internal setting. This may be accomplished, for instance, in the optional processes 506 and 510 by the remote configuration and device monitoring system 320 comparing a stored settings signature 325 to a latest settings signature 326, and then generating the warning if the signatures differ from one another.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A device monitoring system, comprising:
   a medical device for use with a patient, the medical device including:
      an external defibrillator including:
         an input configured to receive an internal setting of the external defibrillator,
         a settings signature unit configured to generate a settings signature indicative of the internal setting,
         an energy storage module configured to store energy for an electrical shock to a patient, and
         defibrillation electrodes configured to receive the stored energy from the energy storage module and provide a shock to the patient, and
      a communication module configured to receive data outside the medical device, send data to the input of the external defibrillator, and receive the settings signature from the external defibrillator and communicate the settings signature out of the medical device; and
   a setup facility configured to transfer the internal setting of the external defibrillator to the medical device.

2. The device monitoring system of claim 1, further including a processor configured to specify a particular setup configuration of the internal setting of the medical device and transmit the data identifying the particular setup configuration to the setup facility.

3. The device monitoring system of claim 1, wherein the setup facility is further configured to transfer the internal setting of the external defibrillator to the medical device via the input of the external defibrillator.

4. The device monitoring system of claim 1, wherein the setup facility is further configured to transfer the internal setting of the external defibrillator to the medical device via the communication module.

5. The device monitoring system of claim 1 in which the communication module is further configured to output the settings signature periodically.

6. The device monitoring system of claim 1 in which the settings signature unit periodically generates the settings signature.

7. The device monitoring system of claim 1 in which the communication module is further configured to output the settings signature based on an event at the medical device.

8. The device monitoring system of claim 1 in which the settings signature unit generates the settings signature based on an event at the medical device.

9. The device monitoring system of claim 1 in which the medical device further includes a first memory to store the settings signature, and the device monitoring system includes a second memory configured to store an expected settings signature.

10. The device monitoring system of claim 1 in which the medical device is further configured to communicate the settings signature in a data packet that includes patient data, and the device monitoring system further comprising a data parser configured to parse the patient data and the settings signature from the data packet and output the settings signature to the processor.

11. The device monitoring system of claim 1 in which the communication module is further configured to receive data.

12. The device monitoring system of claim 11 in which the settings signature unit is further configured to generate the settings signature based on a particular setup configuration.

13. The device monitoring system of claim 1 in which the internal setting identifies a protocol of the external defibrillator.

14. The device monitoring system of claim 1 in which the medical device further includes a component configured to administer a treatment to the patient, or receive data of the patient, or both, the component configured to operate according to the internal setting.

15. The device monitoring system of claim 14 in which the component may be permissively accessed and the internal setting enables or disables the permissive access.

16. The device monitoring system of claim 14 in which the component is an energy delivery component and the internal setting sets an energy delivery level.

17. The device monitoring system of claim 14 in which the component is a patient analyzer and the internal setting determines whether the patient analyzer is set to analyze a patient without user action.

18. The device monitoring system of claim 14 in which the component is a Cardio Pulmonary Resuscitation timer and the internal setting determines a duration.

19. The device monitoring system of claim 14 in which the component is a pacer and the internal setting describes a pacing rate.

20. The device monitoring system of claim 14 in which the component is a metronome and the internal setting determines a metronome schedule.

21. The device monitoring system of claim 14 in which the component is a pacer and the internal setting identifies a pacer current.

22. The device monitoring system of claim 14 in which the component is a data transmitter the internal setting describes a channel or address for transmission of data.

23. The device monitoring system of claim 14 in which the component is a carbon dioxide monitor and the internal setting describes the units of measure for the carbon dioxide monitor.

24. The device monitoring system of claim 14 in which the component is a blood pressure monitor and the internal setting describes an initial pressure level.

25. The device monitoring system of claim 14 in which the component is an alarm and the internal setting includes an alarm volume setting.

26. The device monitoring system of claim 14 in which the internal setting determines whether patient data will be transferred without user action.

27. The device monitoring system of claim 14 in which the component is a patient monitoring lead and the internal setting determines how many data channels exist through the patient monitoring lead.

28. The device monitoring system of claim 14 in which the component is an ECG display, and in which the internal setting includes an operation mode of the ECG display.

29. The device monitoring system of claim 14 in which the internal setting further includes a selection of a display unit of an ECG display.

30. The device monitoring system of claim 14 in which the component is a printer, and in which the internal setting includes a printer operation mode.

* * * * *